United States Patent
D'Ottone

(10) Patent No.: US 7,045,096 B2
(45) Date of Patent: May 16, 2006

(54) STERILIZATION AND DETOXIFICATION OF CONFINED SPACES

(75) Inventor: Luca D'Ottone, Key Biscayne, FL (US)

(73) Assignee: Argentara Five, Inc., Key Biscayne, FL (US)

(*) Notice: Subject to any disclaimer, the term of this patent is extended or adjusted under 35 U.S.C. 154(b) by 759 days.

(21) Appl. No.: 09/683,445

(22) Filed: Dec. 31, 2001

(65) Prior Publication Data

US 2003/0133832 A1     Jul. 17, 2003

(51) Int. Cl.
    *A61L 9/00*     (2006.01)

(52) U.S. Cl. .................. 422/29; 96/224; 96/227; 422/4; 422/24; 422/123; 422/186.07

(58) Field of Classification Search ............... 422/24, 422/4, 29, 121, 123; 96/224, 227
See application file for complete search history.

(56) References Cited

U.S. PATENT DOCUMENTS

| | | | |
|---|---|---|---|
| 5,120,512 A | 6/1992 | Masuda | 422/220 |
| 5,213,759 A * | 5/1993 | Castberg et al. | 422/24 |
| 5,635,059 A * | 6/1997 | Johnson | 210/192 |
| 5,783,242 A | 7/1998 | Teague | 426/320 |
| 5,935,525 A * | 8/1999 | Lincoln et al. | 422/121 |
| 5,951,948 A | 9/1999 | Duroselle et al. | 422/33 |
| 5,953,525 A * | 9/1999 | Glaser et al. | 717/105 |
| 5,961,920 A * | 10/1999 | Soremark | 422/24 |
| 6,066,348 A | 5/2000 | Yuan et al. | 426/236 |
| 6,120,822 A | 9/2000 | Denvir et al. | 426/320 |
| 6,276,304 B1 | 8/2001 | Tai | 119/448 |
| 6,589,489 B1 * | 7/2003 | Morrow et al. | 422/186.3 |
| 6,630,105 B1 * | 10/2003 | O'Neill et al. | 422/24 |
| 2003/0101700 A1 * | 6/2003 | Burdine et al. | 55/385.2 |

OTHER PUBLICATIONS

Hermann et al., "Decontamination of chemical and biological warfare (CBW) agents using an atmospheric pressure plasma jet (APPJ)*'", Physics of Plasma, vol. 6, No. 5, May 1999, pp. 2284-2289.*

* cited by examiner

*Primary Examiner*—Krisanne Jastrzab
(74) *Attorney, Agent, or Firm*—Richard D. Fuerle

(57) ABSTRACT

Pathogens, toxins, and some chemical warfare agents inside an enclosure are destroyed using hydroxyl free radicals. The hydroxyl free radicals can be generated by, for example, reacting ozone with water in the presence of ultraviolet light or reacting hydrogen with nitrogen dioxide in the presence of ultraviolet light.

20 Claims, 1 Drawing Sheet

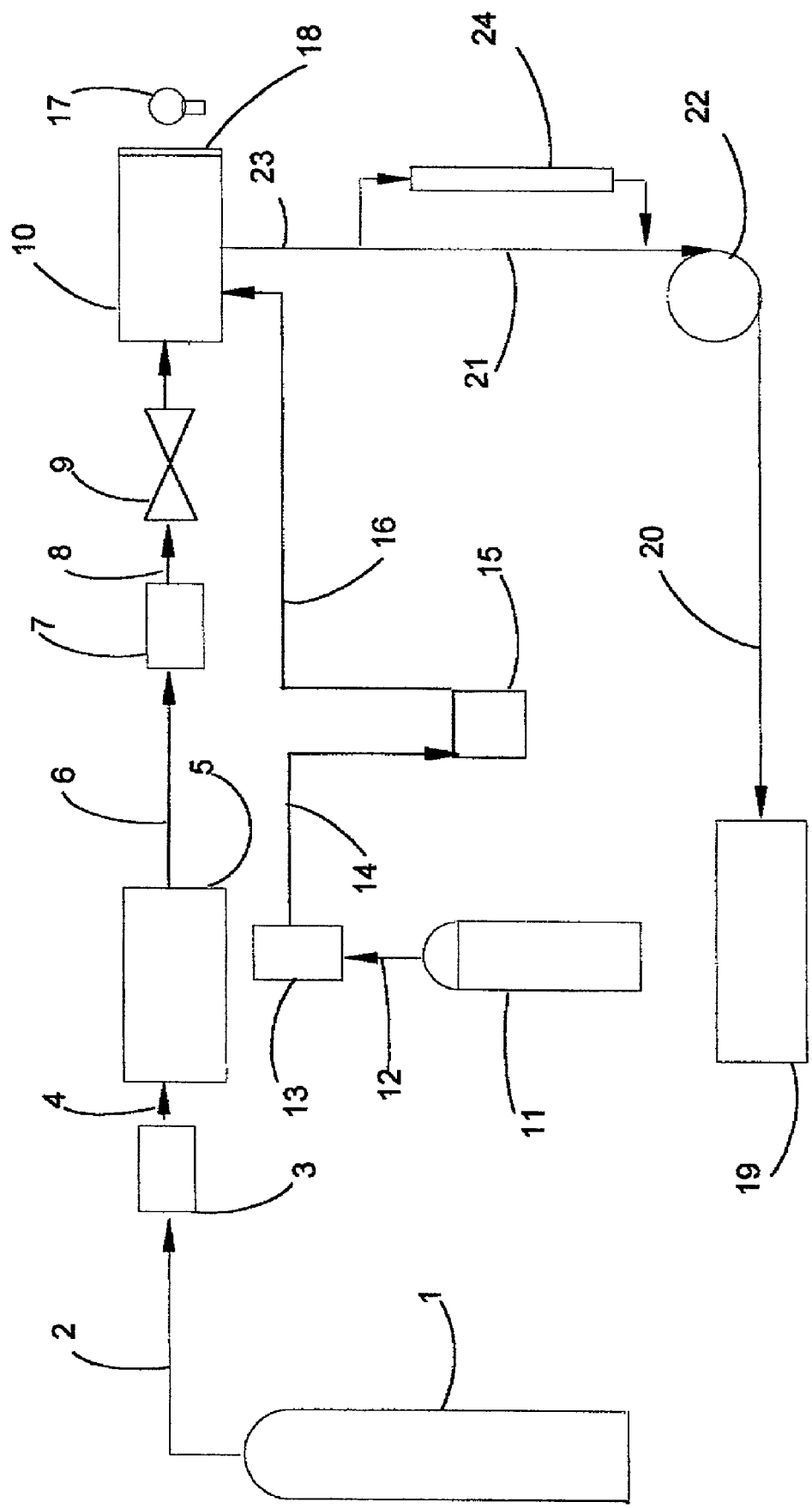

STERILIZATION AND DETOXIFICATION OF CONFINED SPACES

BACKGROUND OF INVENTION

This invention relates to a method and apparatus for sterilizing and detoxifying confined spaces using hydroxyl free radicals. In particular, it relates to exposing ozone and a hydrogen atom donor to ultraviolet light (UV) to generate hydroxyl free radicals, which kill microorganisms and degrade toxic chemicals inside an enclosure.

The recent dissemination of anthrax through the mails has created a need to sterilize mail rooms and offices. For example, anthrax found in the Senate Office Building was killed using chlorine dioxide, a highly toxic gas, followed by sulfite to destroy the chlorine dioxide. However, chlorine dioxide can react with organic compounds to form chlorinated organic compounds that remain in the room and may be carcinogenic. Moreover, the disinfection was not successful and liquid bleach had to be used to remove the last traces of anthrax and anthrax spores. Thus, chlorine dioxide is not entirely satisfactory for this purpose.

Ozone has also been used to sterilize enclosed spaces. When microorganisms are exposed to ozone, the ozone passes into the organisms, attacking their DNA, and killing them. Unlike chlorine dioxide, ozone forms oxygen a few hours after it is used and is not known to form carcinogenic organic compounds unless the organic compound is chlorinated. While ozone is a potent oxidant, in sufficiently high concentrations it may be dangerous to human life.

The presence of toxic chemicals, such as a nerve gas, in buildings or other enclosed spaces is also a concern and substances that are effective against pathogens may not degrade chemical warfare agents.

SUMMARY OF INVENTION

In this invention, hydroxyl free radicals (HO.) are used to sterilize and detoxify enclosed spaces. Hydroxyl free radicals are more effective oxidants than molecular ozone and therefore less is needed to obtain the same degree of effectiveness. Hydroxyl free radicals not only kill most microorganisms, but also degrade many toxic chemicals. Moreover, they are not known to react with organic compounds to form carcinogens and, because they are highly reactive with organics, they are quickly gone, usually within minutes.

The equipment required to practice this invention is relatively inexpensive and the reactants required are common and inexpensive, such as air and water. Because the reactants used are gaseous, the objects to be sterilized do not contact liquids that could damage them. The process can be performed without an operator contacting any hazardous material. If ozone is used to generate the hydroxyl free radicals, any free ozone that reacts with organics forms mainly aldehydes which are quickly photolyzed and removed from the atmosphere.

BRIEF DESCRIPTION OF DRAWINGS

The accompanying drawing is a diagram illustrating a certain presently preferred embodiment of the sterilizing and detoxifying apparatus and process of this invention.

DETAILED DESCRIPTION

In the drawing, oxygen in tank 1 flows through line 2 to flow controller 3, which controls the amount of oxygen that flows through line 4 into ozonizer 5, where it is converted into ozone. Ozonizers are commercially available and convert oxygen into ozone according to the reaction $3O_2 \rightarrow 2O_3$ by, for example, exposing oxygen to UV light or by exposing molecular oxygen to extremely high voltages in a corona discharge. The ozone flows through line 6 into flow meter 7, which measures the amount of gas passing through line 6. The gas then flows through line 8, which has a needle valve 9 in it to control the flow, then into enclosure 10, which contains the pathogens or toxins to be destroyed. (If enclosure 10 is under greater than atmospheric pressure, the ozone is pumped into enclosure 10 and a second flow controller having a safety valve on it (not shown) is used in line 6.)

Tank 11 provides compressed air, which flows through line 12 to flow controller 13. The air goes through line 14 to water vapor bubbler 15, where it picks up water vapor, then through line 16 to enclosure 10 where the water vapor mixes with the ozone. An ultraviolet (UV) lamp 17 provides a source of UV radiation inside enclosure 10, which has an UV transparent window on the side next to UV lamp 17. Window 18 can be coated on the inside with an ozone-resistant UV-transparent coating. UV lamp 17 can also be placed inside the enclosure. The UV light causes the ozone and water vapor to react to form hydroxyl free radicals. Pump 19 draws a partial vacuum on lines 20 and 21, causing residual ozone in enclosure 10 to flow through line 21 to ozone destroyer 22, which can be, for example, a cold trap or warmed copper tubing. A catalytic filter system can also be used to destroy the ozone and collect the airborne particles leaving the enclosure. A small portion of the residual ozone in line 21 enters line 23 and UV cell 24, where the concentration of ozone in line 20 is measured so that the concentration of ozone in enclosure 10 can be calculated.

Because the hydroxyl free radicals have a short lifetime, they are generated inside the enclosure. As the hydroxyl free radicals are being generated, their concentration gradually increases. While the concentration of hydroxyl free radicals in the enclosure and the amount of time needed to detoxify its contents will depend upon the type and quantity of pathogens and toxins in the enclosure and the temperature and humidity used, a minimum concentration of hydroxyl free radicals of about $10^{12}$ molecules/cc is usually needed for sterilization and detoxification and concentrations greater than about $10^{18}$ molecules/cc are difficult to achieve. A preferred concentration range is at least about $10^{16}$ hydroxyl free radicals per $cm^3$ at room temperature and 1 atm. The ozone concentration inside the enclosure, which is directly proportional to the hydroxyl free radical concentration, can be monitored using UV spectroscopy (e.g., a mercury lamp, a photomultiplier tube, and a 253 nm cutoff filter). Hydroxyl free radical concentrations can be monitored directly by more sophisticated techniques such as resonance fluorescence or UV long path absorption. Once the concentration of hydroxyl free radicals has reached at least the minimum concentration, the inside said enclosure should be maintained at at least that concentration for at least about a minute, and preferably for about 1 to about 10 hours, to ensure that complete sterilization and detoxification have occurred.

The hydroxyl free radicals used in this invention can be generated by a variety of methods. The photolysis of ozone and a hydrogen atom donor, as shown in the drawing, is one such method. In the photolysis of ozone, the UV light forms an excited state of ozone ($O(^1D)$) that reacts with water according to the equation: $O(^1D)+H_2O \rightarrow 2HO$. (Some hydroperoxyl free radicals (HOO.) are also generated and, though less effective than hydroxyl free radicals, they also assist in sterilization and detoxification.) In addition, ozone also reacts directly with a hydrogen atom donor to form hydroxyl (and hydroperoxyl) free radicals. Because that reaction occurs even in the absence of UV light, hydroxyl free radicals can form by that reaction anywhere in the room. Ozone may also dissolve in water droplets and form hydroxyl (and hydroperoxyl) free radicals in the droplets, which are carried by the droplets throughout the enclosure. The molar ratio of ozone to hydrogen atom donor should be about 1:1 to about 10:1 as at lower ratios the hydrogen donor would be in excess in the room and the process would reqire higher exposure times to be effective. At higher ratios, an excess of ozone would be available but not effectively employed. The preferred molar ratio of ozone to hydrogen atom donor is about 5:1 to about 10:1. Suitable hydrogen atom donors include water, ammonia, hydrogen gas, methane, and reduced sulfides. The preferred hydrogen atom donor is water because it is inexpensive, safe, and easy to use.

The reaction of ozone with water to form hydroxyl free radicals peaks at a wavelength shorter than 305 nm, so the UV light should have a wavelength of less than about 300 nm. The preferred wavelength is about 100 to about 300 nm and most preferably at about 253 nm because inexpensive commercial UV lamps produce light that peaks at that wavelength. The conversion of ozone and water to hydroxyl free radicals from ozone and water is somewhat limited by the amount of UV radiation produced, but an intensity of a few µ-Joules per $cm^2$ per mole of ozone is usually sufficient; the preferred light intensity is about 1 m-Joule/$cm^2$ per mole of ozone and intensities between 1 µ-Joule and 1 Joule/$cm^2$ per mole of ozone may be used proficiently. The UV lamp that provides the light is preferably positioned so that the ozone and hydrogen atom donor mix and pass in front of the light as they enter the enclosure.

Hydroxyl free radicals can also be generated by exposing a mixture of hydrogen and nitrogen dioxide to UV light, which forms hydroxyl free radicals according to the overall equation: $H_2+NO_2 \rightarrow HO\exists+NO$. Unless the molar ratio of hydrogen to nitrogen dioxide is 1:1 there will be excess hydrogen or nitrogen dioxide, but a practical molar ratio is about 0.9:1 to about 1.1:1.

While the invention is effective at room temperature, to reduce the rate at which the ozone spontaneously decomposes into oxygen it is preferable, if possible, to lower the temperature of the inside of the enclosure. This can be done, for example, by air conditioning or by releasing a cold gas inside the room, as by evaporating liquid nitrogen. A temperature range of about 0 to about 70° C. can be used but about 0 to about 15° C. is preferred.

A high relative humidity (RH) also increases the effectiveness of the invention as water droplets can deliver highly concentrated solutions of hydroxyl free radicals throughout the enclosure. A high RH can be achieved by, for example, using a humidifier or a water bubbler. A RH of about 10 to about 40% is preferred.

To sterilize and detoxify the contents of a large enclosure, such as a room, people and objects in the enclosure that may be damaged by the free radicals are removed and treated elsewhere. To prevent pathogens, toxins, and ozone or free radicals from escaping into the atmosphere, it is preferable to completely seal a room prior to treatment. However, in many cases this may not be practical. In such cases, it is preferable to pump out some of the air in the room so that the room is under a partial vacuum of about 200 to about 750 Torr. The air pumped out can be sterilized and detoxified in a separate enclosure. If desired, the temperature inside the room is lowered and the RH raised. After detoxification, the air in the room is released as fresh air is added.

To sterilize and detoxify small objects, such as mail or supplies, they can be placed inside a sealed container and the free radicals can be generated inside of the container until its contents are rendered harmless. Preferably, a slow flow of hydroxyl free radicals is maintained through the container to provide a residence time of hydroxyl free radicals inside the container of about 1 to about 60 minutes.

This invention is useful against most, if not all, microorganisms, including those that are harmful to humans and animals, such as the pathogens that cause smallpox, anthrax, plague, botulism, tularemia, and hemorrhagic fever. Examples of such pathogens include viruses such as herpes simplex and HIV; bacteria such as Bacillum anthracis, Escherichia coli, Enterobacter cloacae, Klesibella pneumoniae, Salmonella typhimurium, Salmonella schottmulleri, Salmonella choleraesuis, Salmonella enteritidis, Staphylococcus aureus, Streptococcus faecalis, Vibrio cholerae, Clostridium botulinum, and Colostridium perfringens; fungi such as Aspergillus flavus, Aspergillus ochraceus, Penicillium toxicarium, and Fusarium graminearum; and single-celled organisms such as amoebae. Hydroxyl free radicals may also destroy pions prions, fungus spores, various parasites, and many chemical warfare agents such as phosgene and mustard gas.

The invention claimed is:

1. Apparatus for sterilizing and detoxifying the inside of an enclosure comprising
   (A) means for sealing said enclosure;
   (B) means for generating a concentration of hydroxyl free radicals inside said sealed enclosure of at least about $10^{16}$ molecules/cc for at least 1 minute without any person entering the said enclosure;
   (C) a pump for pumping gas out of said enclosure; and
   (D) means for detoxifying gas pumped out of said enclosure.

2. Apparatus according to claim 1 wherein said means for generating hydroxyl free radicals is an ozonizer, a hydrogen atom donor, an ultraviolet lamp, and means for mixing said ozone and said hydrogen atom donor and exposing said mixture to light from said ultraviolet lamp.

3. Apparatus according to claim 2 wherein said ozonizer is outside said enclosure and said hydroxyl free radicals are generated inside said enclosure.

4. Apparatus according to claim 2 wherein said hydrogen atom donor is water vapor.

5. Apparatus according to claim 1 wherein said means for generating hydroxyl free radicals is hydrogen gas, nitrogen dioxide gas, an ultraviolet lamp, and a means for mixing and releasing them inside said enclosure.

6. Apparatus according to claim 1 including means for maintaining the inside of said enclosure at a temperature of about 0 to about 15° C.

7. Apparatus according to claim 1 including means for maintaining the relative humidity inside said enclosure at about 10 to about 40%.

8. Apparatus according to claim 1 wherein said means for detoxifying said gas is a cold trap.

9. Apparatus according to claim 1 wherein said enclosure contains Bacillus anthracis.

10. A method of detoxifying the inside of an enclosure using an apparatus according to claim 1 comprising
   (A) sealing said enclosure;
   (B) generating said hydroxyl free radicals and releasing them inside said enclosure at a concentration of at least about $10^{16}$ molecules/cc for at least 1 minute without any person entering said enclosure;
   (C) pumping gas out of said enclosure; and
   (D) detoxifying said gas.

11. A method according to claim 10 wherein said hydroxyl free radicals are generated by reacting ozone with water in the presence of ultraviolet light.

12. A method according to claim 10 wherein said hydroxyl free radicals are generated by reacting hydrogen with nitrogen dioxide in the presence of ultraviolet light.

13. Apparatus for detoxifying the inside of an enclosure containing pathogens comprising
   (A) means for sealing said enclosure;
   (B) an ultraviolet lamp for generating ultraviolet light at a wavelength of less than about 300 nm;
   (C) an ozonizer outside of said enclosure, for generating ozone from air;
   (D) a source of water vapor; and
   (E) means for mixing said ozone with said water vapor in a molar ratio of about 1:1 to about 10:1 and exposing said mixture to said ultraviolet radiation inside said enclosure, said apparatus generating a concentration of hydroxyl free radicals inside said enclosure of at least about $10^{16}$ molecules/cc for at least about 1 hour without any person entering said enclosure,
   (F) a pump for pumping gas out of said enclosure; and
   (G) means for detoxifying gas pumped out of said enclosure.

14. Apparatus according to claim 1 including means for producing a partial vacuum within said sealed enclosure of about 200 to about 750 Torr.

15. Apparatus according to claim 13 wherein said UV light can generate at least about 1 μ-Joule/cm$^2$ of ultraviolet light per mole of said ozone at a wavelength of about 100 to about 300 nm.

16. A method of detoxifying the inside an enclosure using an apparatus according to claim 13 comprising
   (A) sealing said enclosure;
   (B) generating ozone with said ozonizer;
   (C) turning on said ultraviolet lamp;
   (D) mixing said ozone and water vapor at a molar ratio of about 1:1 to about 10:1; and
   (E) exposing said mixture to said ultraviolet light inside said enclosure, whereby hydroxyl free radicals are formed at a concentration of at least about $10^{16}$ molecules/cc for at least about 1 hour without any person entering said enclosure;
   (F) pumping gas out of said enclosure; and
   (G) detoxifying said gas.

17. A method according to claim 16 including the step of producing a partial vacuum within said sealed enclosure of about 200 to about 750 Torr.

18. A method according to claim 16 wherein the relative humidity inside said enclosure is about 10 to about 40% and the temperature inside said enclosure is about 0 to about 15° C.

19. Apparatus for sterilizing the inside of an enclosure containing pathogens comprising
   (A) means for sealing said enclosure;
   (B) an ultraviolet lamp for generating ultraviolet light at a wavelength of less than about 300 nm;
   (C) a source of hydrogen gas and a source of nitrogen dioxide gas;
   (D) means for mixing said hydrogen gas with said nitrogen dioxide gas in a molar ratio of about 0.9:1 to about 1.1:1 outside said enclosure and exposing said mixture to said ultraviolet light inside said enclosure, said apparatus generating a concentration of hydroxyl free radicals inside said room of at least about $10^{16}$ molecules/cc for at least about 1 hour without any person entering said enclosure;
   (E) a pump for pumping gas out of said enclosure; and
   (F) means for detoxifying said gas.

20. A method of sterilizing the inside an enclosure using an apparatus according to claim 19 comprising
   (A) sealing said enclosure;
   (B) mixing said hydrogen gas and said nitrogen dioxide gas at a molar ratio of about 0.9:1 to about 1.1:1;
   (C) exposing said mixture to said ultraviolet light, whereby hydroxyl free radicals are formed inside said enclosure at a concentration of at least about $10^{16}$ molecules/cc for at least about 1 hour without any person entering said enclosure;
   (D) pumping gas out of said enclosure; and
   (E) detoxifying said gas.

* * * * *